(12) United States Patent
Feng

(10) Patent No.: US 7,599,135 B2
(45) Date of Patent: Oct. 6, 2009

(54) HANDHELD MAGNIFYING DEVICE INCORPORATING A CIRCULAR ARRAY OF LIGHT EMITTING DIODES

(76) Inventor: Duan Feng, Unit 30C, Hai Tao Block, Seaview Garden, Overseas China Town, Shenzhen (CN)

( * ) Notice: Subject to any disclaimer, the term of this patent is extended or adjusted under 35 U.S.C. 154(b) by 0 days.

(21) Appl. No.: 12/231,357

(22) Filed: Sep. 2, 2008

(65) Prior Publication Data
US 2009/0067066 A1 Mar. 12, 2009

(30) Foreign Application Priority Data
Sep. 11, 2007 (CN) .................... 2007 2 0170660 U

(51) Int. Cl.
*G02B 27/02* (2006.01)
*G02B 7/02* (2006.01)

(52) U.S. Cl. .................... 359/803; 359/811; 359/819

(58) Field of Classification Search .................. 359/803, 359/813, 811, 819
See application file for complete search history.

(56) References Cited

U.S. PATENT DOCUMENTS 5,479,293 A * 12/1995 Reed ........................ 359/432
7,279,688 B2 * 10/2007 Campman ................ 250/461.1

* cited by examiner

*Primary Examiner*—Ricky L Mack
*Assistant Examiner*—Brandi N Thomas

(57) ABSTRACT

An LED-assisted magnifying device having a generally circularly-shaped array of LEDs adapted to provide a uniform pattern of visible illumination below a magnifying lens. An ultraviolet LED is provided as an alternate, optional light source to the generally circularly-shaped array of LEDs. A darkfield illuminator may be advantageously employed with the LED-assisted magnifying device when gemstones are being inspected.

5 Claims, 10 Drawing Sheets

HANDHELD MAGNIFYING DEVICE INCORPORATING A CIRCULAR ARRAY OF LIGHT EMITTING DIODES

CROSS-REFERENCE TO RELATED APPLICATIONS

This application claims the benefit of priority to Chinese Patent Application No. 200720170660.X filed Sep. 11, 2007.

FIELD OF THE INVENTION

The present invention relates to handheld, portable magnifying device. More particularly, the present invention relates to a magnifying device incorporating a generally circular array of light emitting diodes positioned so as to provide a field of illumination with improved uniformity.

BACKGROUND OF THE INVENTION

Jewelry professionals typically use a handheld monocular, popularly called a loupe, in order to magnify gemstones and other jewelry that they wish to inspect. These loupes have special lenses that allow the viewer's eyes to focus on an object at a much closer distance than is normally possible, making the object appear to be larger and revealing tiny details unseen with normal vision. Loupes are labeled with a number, followed by the symbol "×," which means "times." For example, a 2× loupe makes an object appear two times its actual size and a 5× loupe provides a times-five increase.

In other applications, engineers and technicians will use a loupe to inspect a printed circuit board with small surface components on it. Offset printing sees frequent use of loupes in order to carefully analyze how ink lays on paper. Strippers use loupes in order to register film separations to one another. Pressmen use loupes to check registration of colors, estimate dot-gain, and diagnose issues with roller pressure and chemistry based on the shape of individual dots and rosettes. Photographers use loupes to review, edit or analyze negatives and slides on a light table. Many dentists use loupes to better scrutinize the entities within their patients' mouths in order to make a better diagnosis, for example, to determine how far a crack proceeds along the surface of a tooth. Loupes are also used in order to perform on a more precise level; while dentists drill teeth on a millimeter scale, magnification can enlarge the dentists' view of the teeth, perhaps making it easier to inspect teeth for decay and/or see things that ordinarily would not be seen without magnification.

A 10× loupe having a 10× power of magnification is the standard instrument used to determine a diamond's clarity grade in the gemological industry. While higher-power magnification devices may be used to examine the stone, inclusions (internal flaws) and blemishes (surface irregularities) are not factored into the stone's final clarity grade if they are small enough to be undetectable when the stone is examined under 10× magnification. Loupes with black framing around the lens are preferable because black eliminates reflections that can alter the color of the object being viewing.

Loupes made with a single lens are generally of poor quality, distorting the object you're magnifying and adding flashes of color to it. A triplet loupe is a magnifier that contains three lenses placed together in such a way that distortion and color problems are corrected. The distance the loupe is held from an object in order to best the best focus and magnification is the focal length of a loupe and generally decreases as loupe magnification increases. The size of the area viewable through the lens is the field of view. The diameter of the lens affects the field of view as does magnification power—the higher the magnification power the smaller the field of view. The depth of field is related to the distance one can move the loupe towards or away from an item and still have the item in focus. The higher the loupe magnification power, the shorter the depth of field. However, even if these loupe characteristics are optimized, for example in viewing jewelry, without proper illumination, the object being studied will not be clearly visible.

U.S. Pat. No. 4,763,986 discloses an illuminated loupe including a housing having top and bottom covers, a magnifying glass frame pivotally connected between the top and bottom covers and arranged to swing through the covers, a magnifying glass carried by the magnifying glass frame, a light bulb carried by the magnifying glass frame and arranged such that the light therefrom is directed into the frame, and beneath the magnifying glass carried by the frame.

In recent years, semiconductor light emitting diode ("LED") lamps have come into use in flashlights and other applications. LEDs are typically constructed of gallium arsenide (GaAs), gallium arsenide phosphide (GaAsP) gallium phosphide (GaP), or gallium nitride (GaN). The LED light operates on a low current and a negligible amount of heat is produced. Because of their low level of power required for operation, LEDs have been used to provide illumination for loupes.

U.S. Pat. No. 6,483,651 discloses a magnifying lens apparatus containing a magnifying lens mounted to a support housing. The apparatus contains a light emitting diode lamp to provide at least some illumination to an object being magnified by the magnifying lens.

SUMMARY OF THE INVENTION

The present invention provides a dramatic improvement in the usefulness of loupes by providing a LED-assisted magnifying device having a generally circularly-shaped array of a plurality of LEDs adapted to provide a uniform pattern of visible illumination below a magnifying lens. A housing supports the LED illumination source and magnifying lens, a power source for the LEDs and a switch for activating and deactivating the LED illumination source. The housing may be swivelably mounted to an open protective carrier. The attachment for mounting the housing to the carrier allows the housing to move from a "closed-protective" position to an "in-use open" position. In an advantageous embodiment, an ultraviolet LED is provided as an alternate, optional light source to the generally circularly-shaped array of LEDs. The present invention also provides a darkfield illuminator having a second a plurality of LEDs that can be advantageously employed with LED-assisted magnifying device when gemstones are being inspected.

DETAILED DESCRIPTION OF THE PREFERRED EMBODIMENTS

Figure 1:
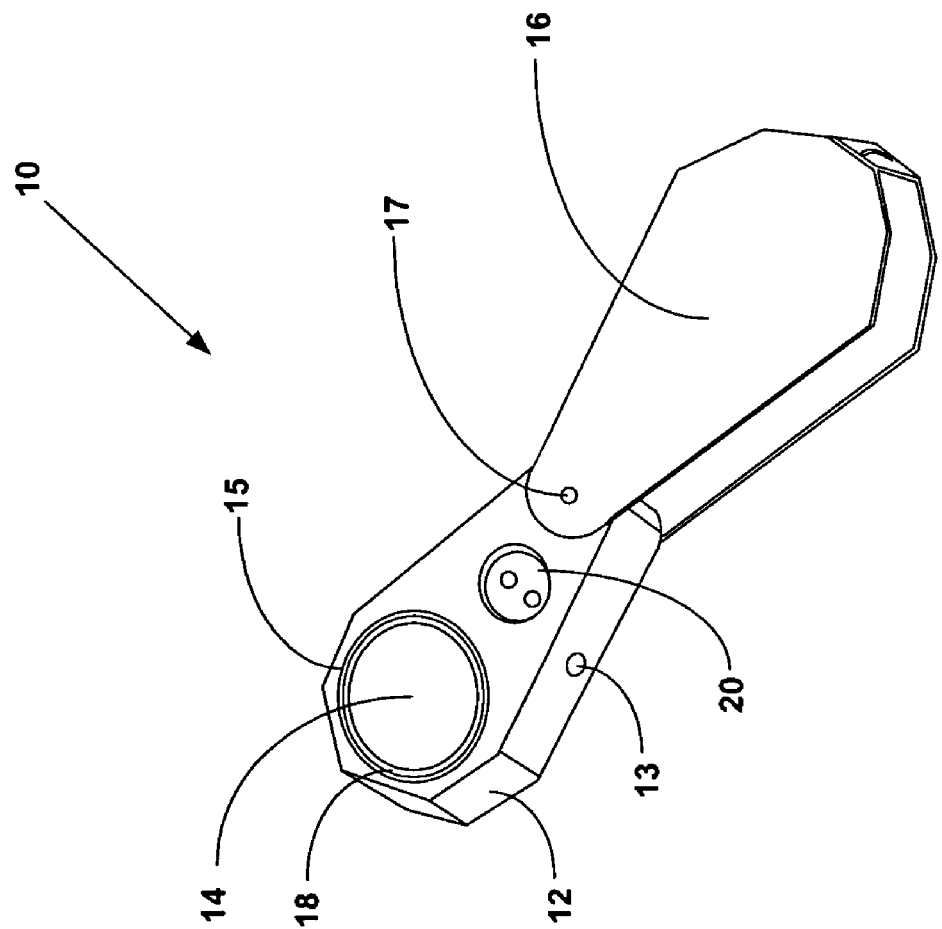
FIG. 1 is a perspective schematic bottom view of the LED-assisted magnifying device of the present invention, showing the lens housing in a open condition.

FIG. 1 shows a perspective schematic bottom view of the LED-assisted magnifying device 10 of the present invention, the LED-assisted magnifying device 10 comprising a lens housing 12 having a magnifying lens assembly 14 mounted in an opening 15, the lens housing 12 being pivotably connected to a similarly shaped, open-sided casing 16 by a pivoting member 17. Optionally, the lens housing 12 may be covered with a circular white acrylic diffusing filter 18 having purposes described hereinafter. The pivoting member 17 is adapted so that lens housing 12 may be rotated from a "closed-protective" position, wherein the housing 12 is enclosed by the casing 16, to an "in-use open" position wherein the housing 12 is rotated outside casing 16.

In an exemplary embodiment, magnifying lens assembly 14 comprises three lenses to correct for aplantic and achromatic aberrations. The aplanatic lens is adapted to maintain a very small focused spot, providing for higher energies at the focal point than can be achieved with singlet lenses. Generally, lens assembly 14 is a biconvex thick lens having concentric spherical lens surfaces whose radii are used to satisfy the aplanatic condition. To minimize chromatic aberration, the biconvex thick lens may be formed of a plurality of cemented elements having indices which are close to each other but having respective different dispersions. Preferably, lens assembly 14 also comprises achromatic lens corrected to bring two wavelengths (typically red and blue) into focus in the same plane. Such lens are made from glasses with different amounts of dispersion. Usually one element is a concave lens made out of flint glass, which has relatively high dispersion, while the other, convex, element is made of crown glass, which has lower dispersion. The lens elements are mounted next to each other, typically cemented together, and shaped so that the chromatic aberration of one is counterbalanced by that of the other. Preferably, lens assembly 14 is mounted in lightweight metal rim colored black to minimize reflections. Magnification of these lenses ranges from 2.5× to 4× depending on their dimensions and this may be varied depending upon the field of use of magnifying device 10.

In an exemplary embodiment, LED-assisted magnifying device 10 also comprises a power source 20 such as a so-called button-cell battery, a small form-factor battery designed for use in wrist watches, pocket calculators, hearing aids, and similar compact portable electronics products. Advantageously, three of such button-cell batteries are placed in series to provide power source 20. Such power sources 20 are compact and have long life, examples being mercury oxide and silver oxide cells. Common anode materials are zinc or lithium, common cathode materials are manganese dioxide, silver oxide, carbon monofluoride or copper oxide. Power source 20 may have the form of three "stacked" 10 mm button cell batteries, providing about 3-4 hours of continuous use of magnifying device 10. The power source 20 may also be rechargeable and may be stored within housing 12 in an opening or beneath a removable lid for replacing the batteries when necessary. A pair of holes 21 may be provided in order to facilitate removal of such a lid with an appropriate wrench. Further, the housing 12 may have an outlet 13 for recharging battery 20 by means of a connection to an appropriate external source.

Figure 2:
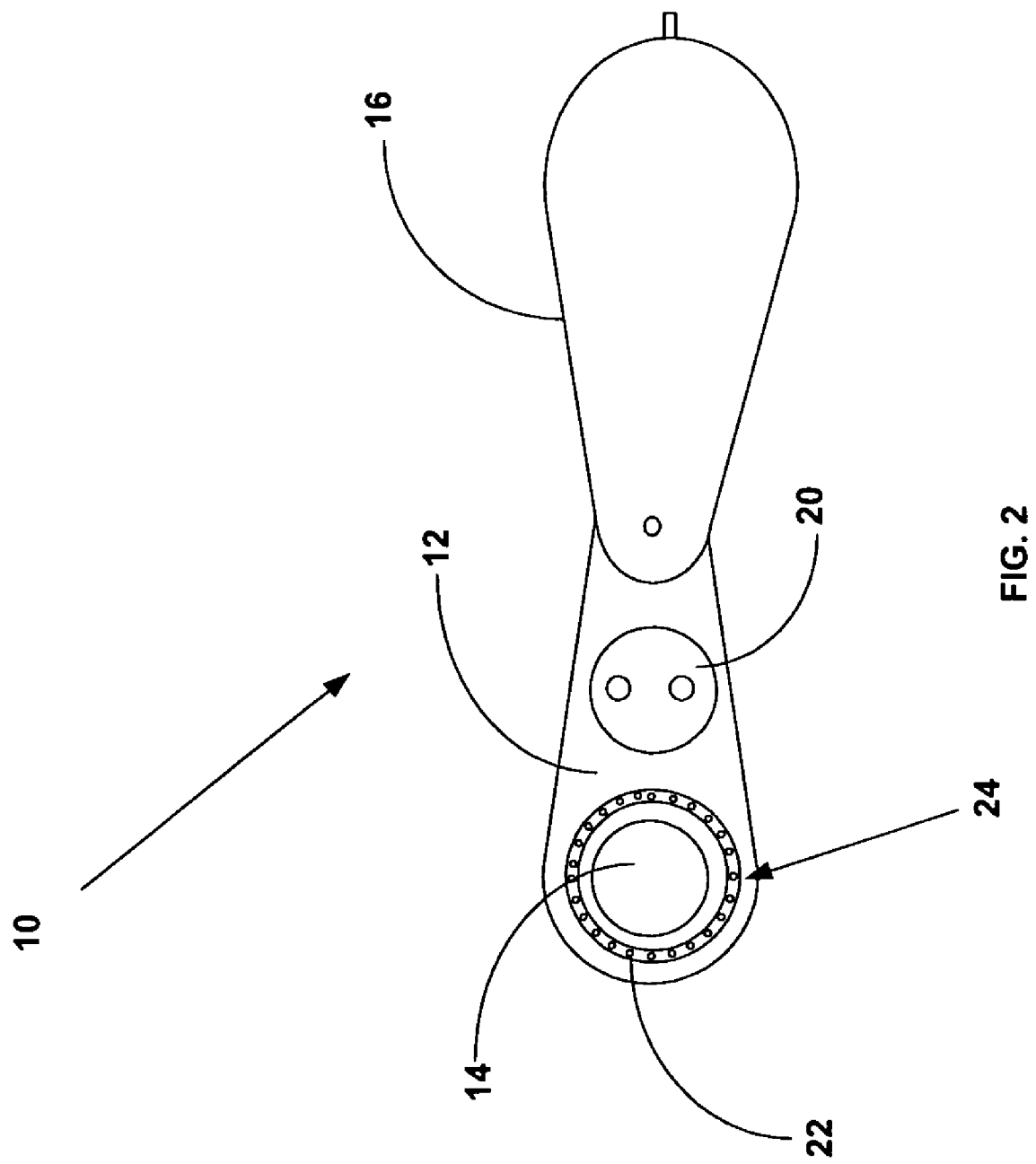
FIG. 2 is a bottom schematic view of the LED-assisted magnifying device of FIG. 1.

FIG. 2 is a bottom view of LED-assisted magnifying device 10 and illustrates a key feature of the present invention, wherein acrylic diffusing filter 18 has been removed to expose a generally circularly-shaped array 24 of a plurality of LEDs 22 that are adapted to provide a uniform pattern of illumination below magnifying lens 14. The actual number of LEDs 22 may be optimized according to the magnifying power of lens assembly 14, wherein a smaller number of LEDs 22 is used for higher power magnification factors. LEDs 22 are conventional, commercially available LEDs 22 made from a variety of inorganic semiconductor materials and the color of the emitted light therefrom depends on the composition and condition of the semiconducting material used. LEDs 22 are available with infrared, visible, or ultraviolet radiation bands, making the following colors commercially available (nm=nanometers):

Aluminum gallium arsenide (AlGaAs)—red and infrared

Aluminum gallium phosphide (AlGaP)—green

Aluminum gallium indium phosphide (AlGaInP)—high-brightness orange-red, orange, yellow, and green Gallium arsenide phosphide (GaAsP)—red, orange-red, orange, and yellow Gallium phosphide (GaP)—red, yellow and green Gallium nitride (GaN)—green, pure green (or emerald green), and blue also white (if it has an AlGaN Quantum Barrier)

Indium gallium nitride (InGaN)—450-470 nm—near ultraviolet, bluish-green and blue Silicon carbide (SiC) as substrate—blue Silicon (Si) as substrate—blue Sapphire (Al2O3) as substrate—blue Zinc selenide (ZnSe)—blue Diamond (C)—ultraviolet—365-420 nm Aluminum nitride (AlN), aluminum gallium nitride (AlGaN), aluminum gallium indium nitride (AlGaInN)—near to far ultraviolet (down to 210 nm)

With this wide variety of colors, circular arrays of multicolor LEDs 22 can be designed to produce conventional or unconventional color patterns, optimized for viewing various types of jewelry. The LED lamps 22 may be chosen having emitted radiation from the variety of colors shown above; in an advantageous embodiment, white light LEDs 22 having an emission temperature in a range centered around 5,500±200 Kelvin. Such LEDs are commercially available from producers such as Lumileds Lighting, San Jose, Calif. and Nichia America Corporation, Mountville, Pa.

Figure 3:
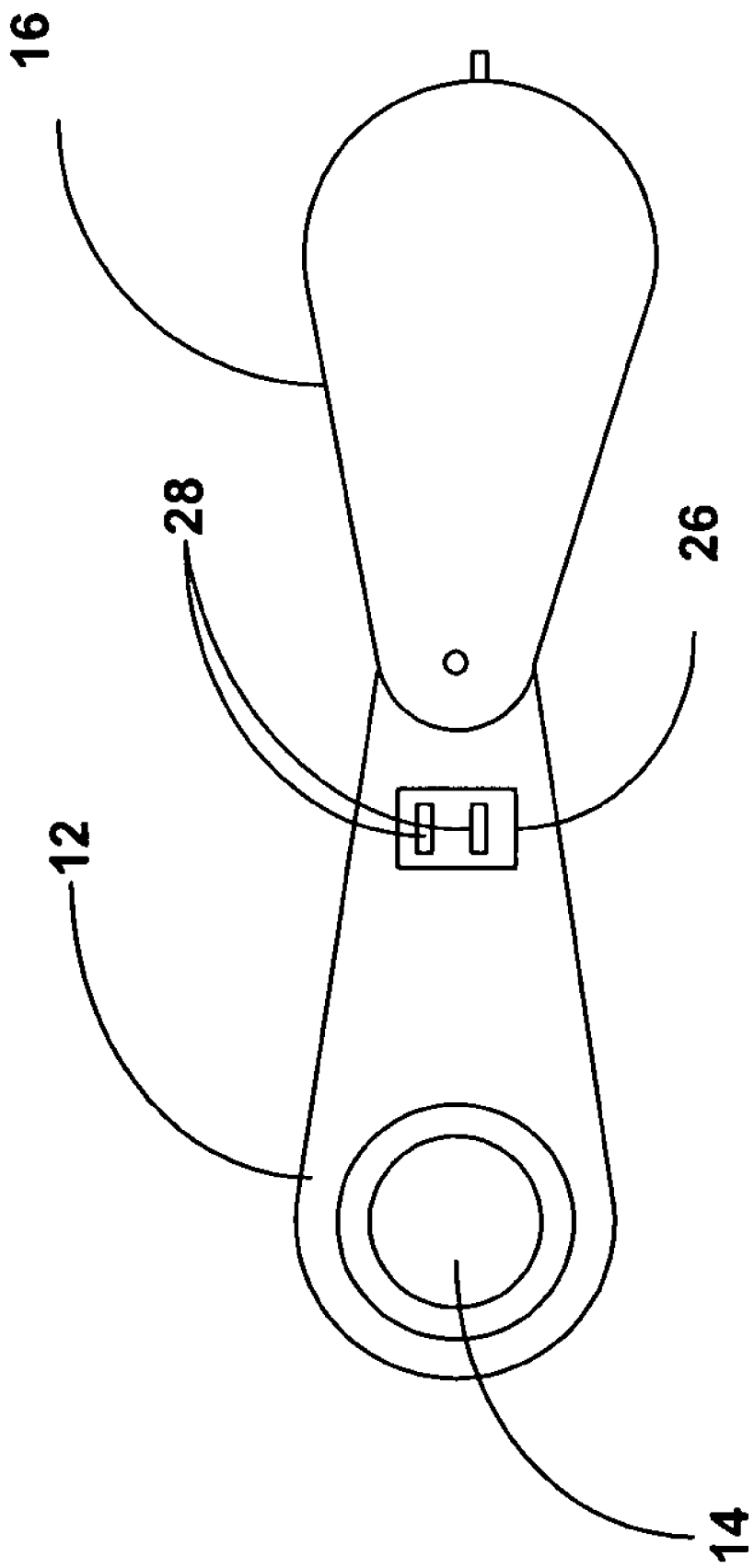
FIG. 3 is a top schematic view of the LED-assisted magnifying device of FIG. 1.

FIG. 3 is a top view of LED-assisted magnifying device 10 and illustrates a power switch 26 for activating the LEDs 22, switch 26 having at least one and maybe more separate light switches 28, of which, one light switch 28 is employed to send electrical current from power source 20 to the circular array 24 of LEDs 22, applying voltage across the individual LEDs and producing a beam of light focused at the focal plane of lens assembly 14.

Figure 4:
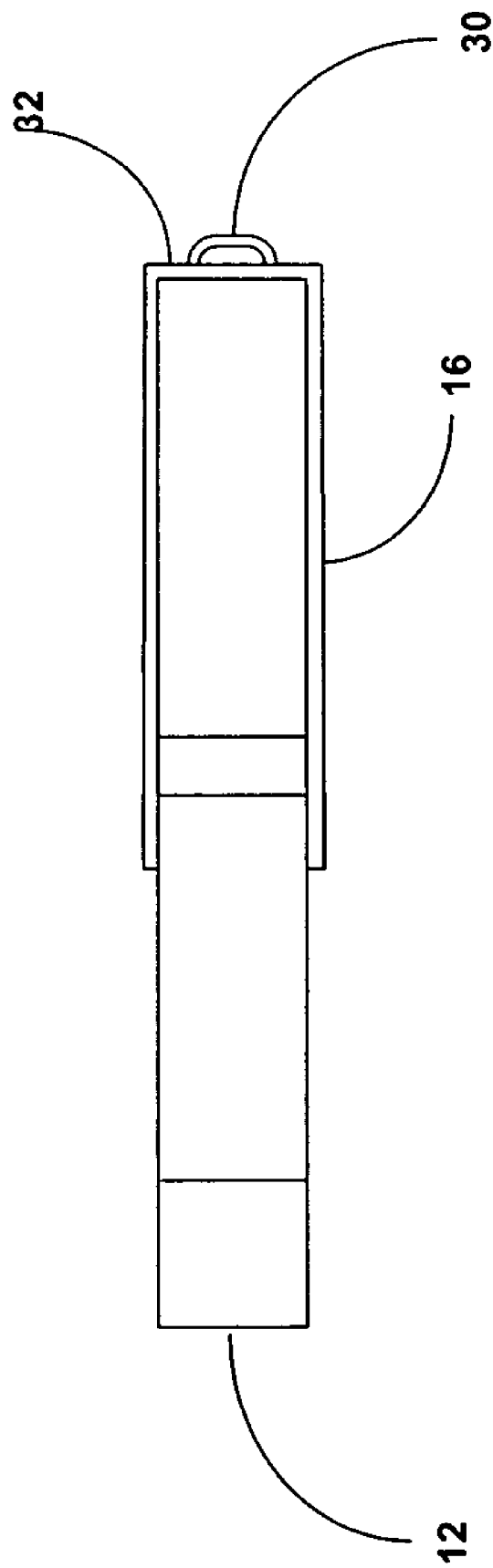
FIG. 4 is a side elevation schematic view of the LED-assisted magnifying device of FIG. 1.

FIG. 4 is a side elevation view of LED-assisted magnifying device 10 and shows the open-sided casing 16 into which lens housing 12 may be rotated "closed" when magnifying device 10 is not in use and from which lens housing 12 may be rotated "open" when it is desired to use magnifying device 10.

For purposes of convenience in attaching a lanyard, a small, open handle 30 is attached to a solid end-wall portion 32 of casing 16.

Figure 5:
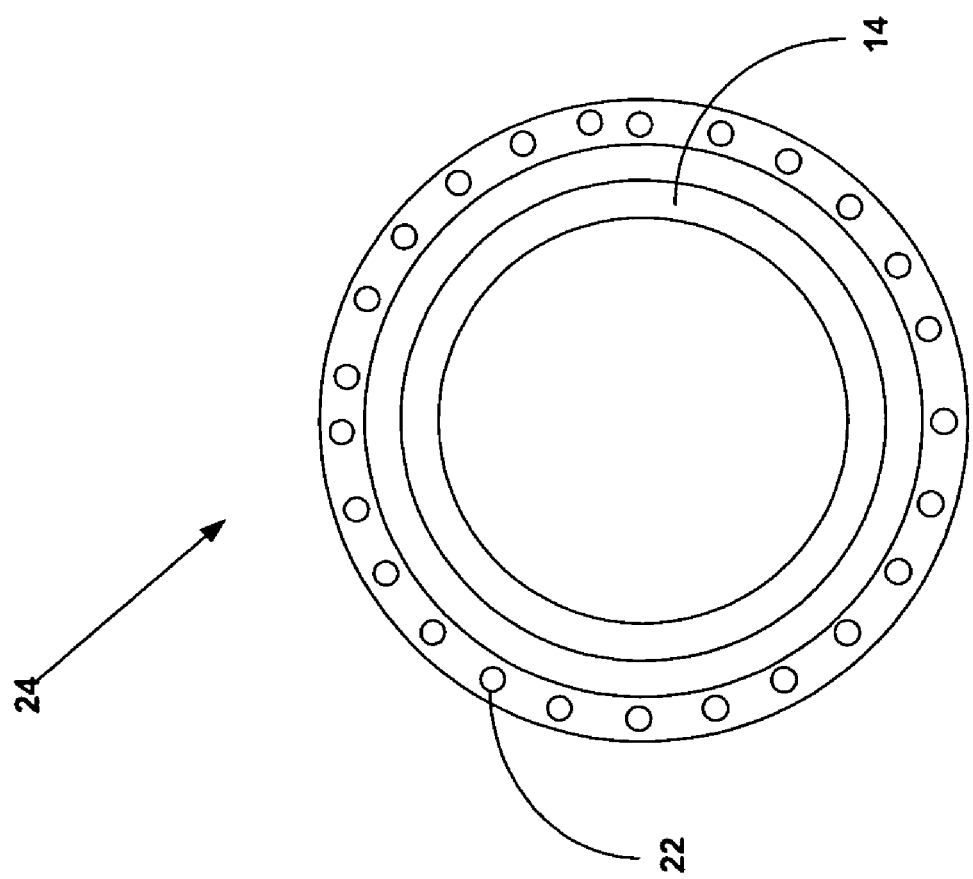
FIG. 5 is an enlarged bottom schematic view of a key feature of the LED-assisted magnifying device of FIG. 1.

FIG. 5 is an enlarged view of the generally circular array 24 of LEDs 22 of the LED-assisted magnifying device of FIG. 1. The generally circular array 24 of LEDs 22 typically "surrounds" the magnifying lens assembly 14 and as explained above is adapted with a plurality of LEDs 22 whose radiation wavelengths may be selected from a variety of different ranges, thereby providing a number of different visible colors. Preferably, the plurality of LEDs 22 are evenly spaced apart within the generally circular array 24. The number of LEDs of any particular visible color may be intermixed with other LEDs of different visible colors to provide a wide variety of single color or mixed color illumination patterns. Preferably the LEDs are selected and mounted so that a plane of maximum illumination is closely coincident with the focal range of magnifying lens assembly 14.

Figure 6:
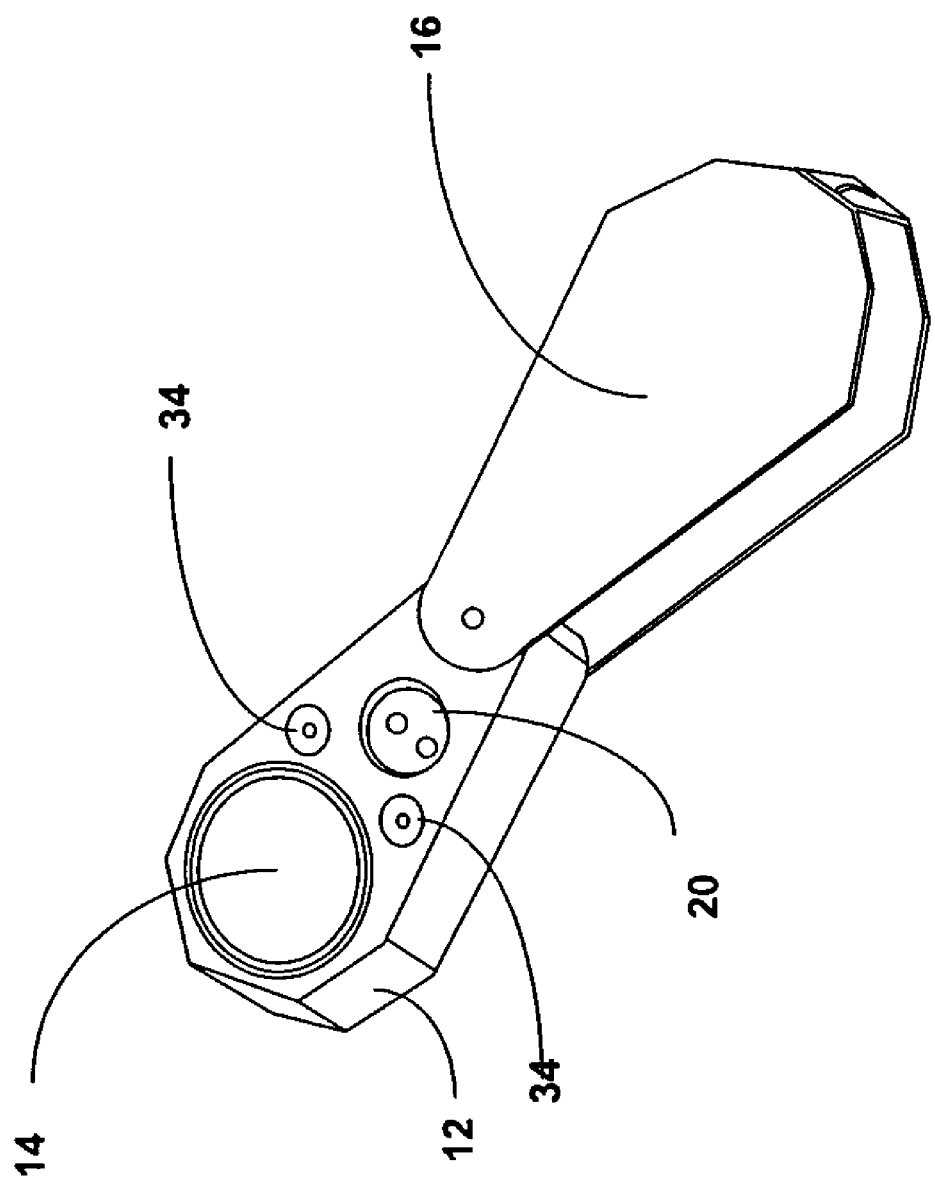
FIG. 6 is a bottom schematic view of an alternate embodiment of the LED-assisted magnifying device of FIG. 1.

FIG. 6 is a bottom view of an alternate embodiment of LED-assisted magnifying device 10 and illustrates another key feature of the present invention, wherein at least one ultraviolet LED 34 is installed in the bottom surface of lens housing 12. In this embodiment, a second one of the light switches 28 in power switch 26 is activated to send electrical current from power source 20 to the ultraviolet LED 34, applying voltage across either one of or both of the individual LEDs 34 and producing a beam of ultraviolet light focused at the focal plane of lens assembly 14. Preferably, the light wavelength range of ultraviolet LED 34 is in the range of about 380-400 nm in order to further assist in examining the fluorescence of gem stones by a jeweler.

One of the most effective ways to improve contrast when a specimen like a gemstone is being inspected by LED-assisted magnifying device 10 is to utilize darkfield illumination. Darkfield illumination is a specialized illumination technique that capitalizes on oblique illumination to enhance contrast in gemstones that are not imaged well under normal brightfield illumination conditions. Darkfield illumination with reflected light enables visualization of grain boundaries, surface defects, and other features within gemstones that are difficult or impossible to detect with brightfield illumination. To obtain darkfield illumination, the zeroth order or direct light is blocked by an opaque stop so that only the peripheral rays of light pass through the gemstone, these rays being at oblique angles and at all azimuths. The rays are diffracted, refracted, and reflected into the LED loupe to form a bright image of a gemstone superimposed onto a dark background.

Figure 7:
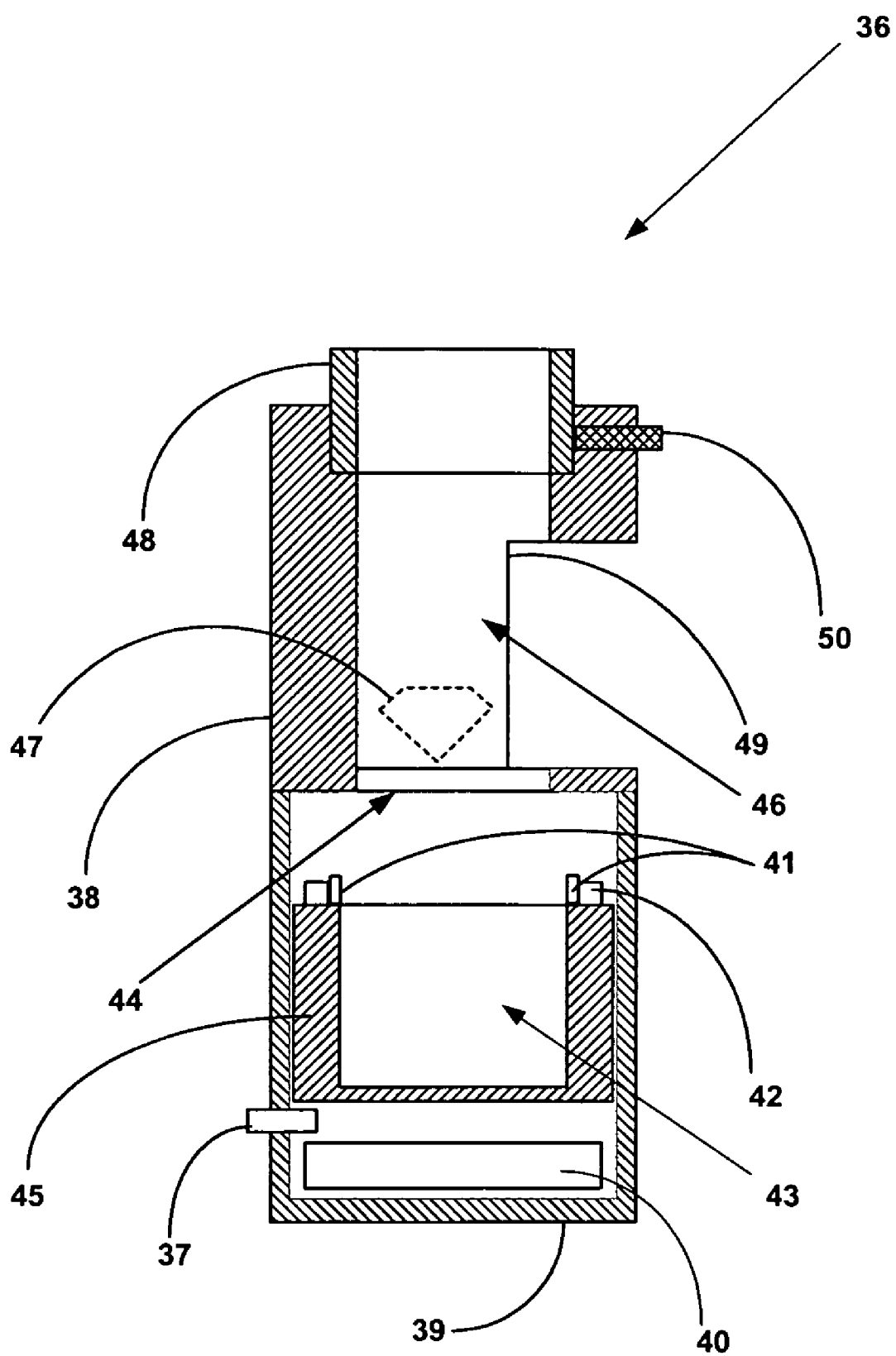
FIG. 7 is a sectional view of a darkfield illuminator that can be advantageously employed with the LED-assisted magnifying device of FIG. 1.

FIG. 7 is a sectional view of a darkfield illuminator 36 that can be advantageously employed with LED-assisted magnifying device 10 when gemstones are being inspected. The use of darkfield illumination in conjunction with LED-assisted magnifying device 10 enables very small internal inclusions to be made visible to the unassisted human eye. Darkfield illuminator 36 comprises a tubular-shaped encasement 38 for containing a gemstone 47 (dashed lines) in an internal, open gemstone compartment 46, the compartment 46 being accessed through an opening 49 in the sidewall of encasement 38. Encasement 38 may be threadably attached at its lower end to a source of darkfield illumination 39, the source of darkfield illumination 39 comprising a conventional, rechargeable battery power source 40 and a source of LED illumination, preferably a circular array of a plurality of LEDs 42 and a connecting switch 37. Illumination from the plurality of LEDs 42 supported atop the perimeter of a cup-like canister 45 passes through an encasement opening 44 in the upper part of the source of illumination 39 into compartment 46 containing gemstone 47 and is reflected at oblique angles and azimuths inside an compartment 46 that is sized to accept gemstones 47 (in dashed lines) for examination by LED-assisted magnifying device 10. An important feature of the source of darkfield illumination 39 is an upwardly extending rim 41 that effectively prevents any illumination from the plurality of LEDs 42 from entering an open darkfield cavity 43 described hereinafter. LED-assisted magnifying device 10 is attached to darkfield illuminator 36 using an adjustable, threaded ring screw 48 that may be constrained at different focal lengths by a lock screw 50.

Figure 7A:
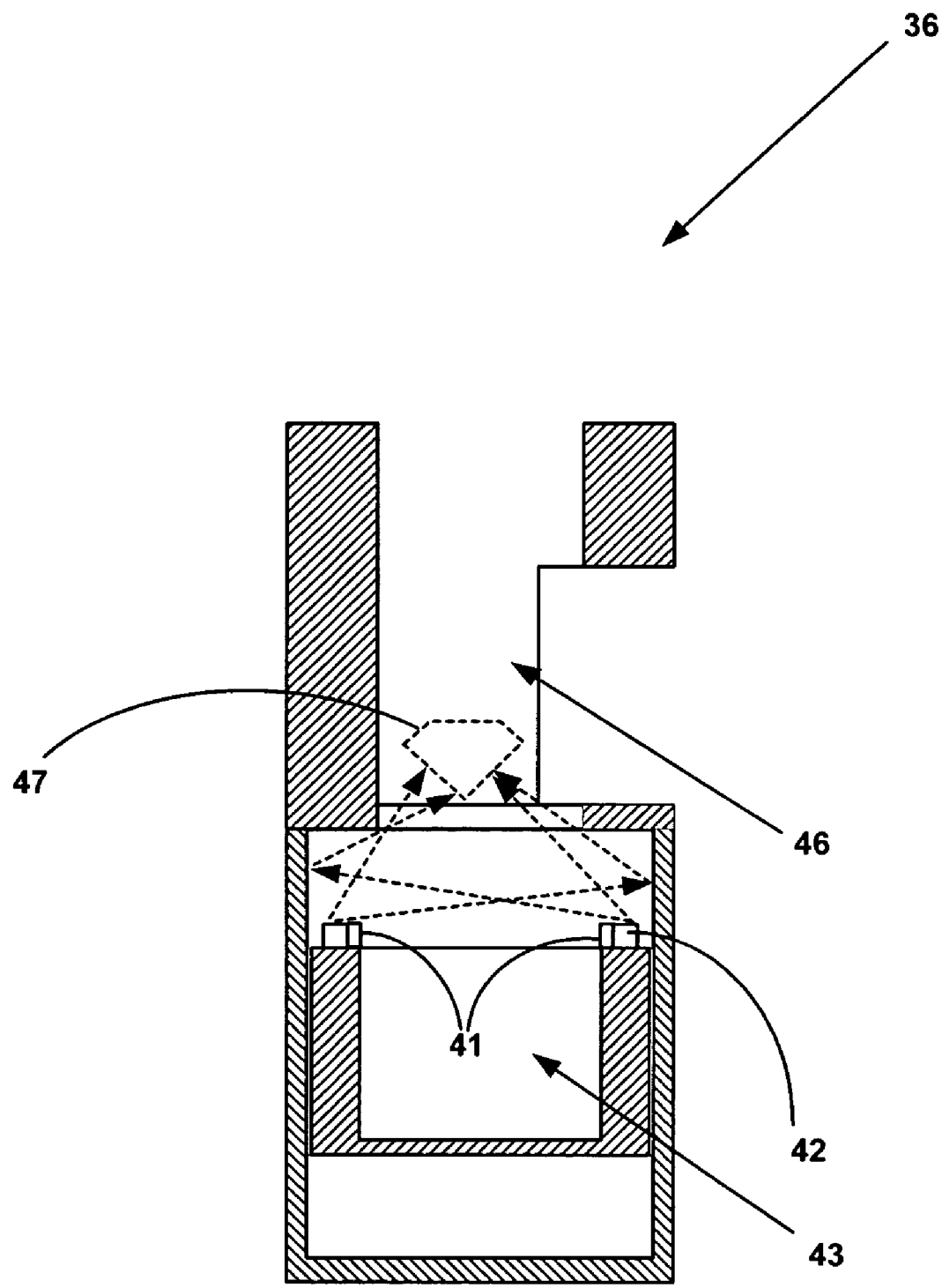
FIG. 7A is a portion of the darkfield illuminator of FIG. 7A.
Figure 8:
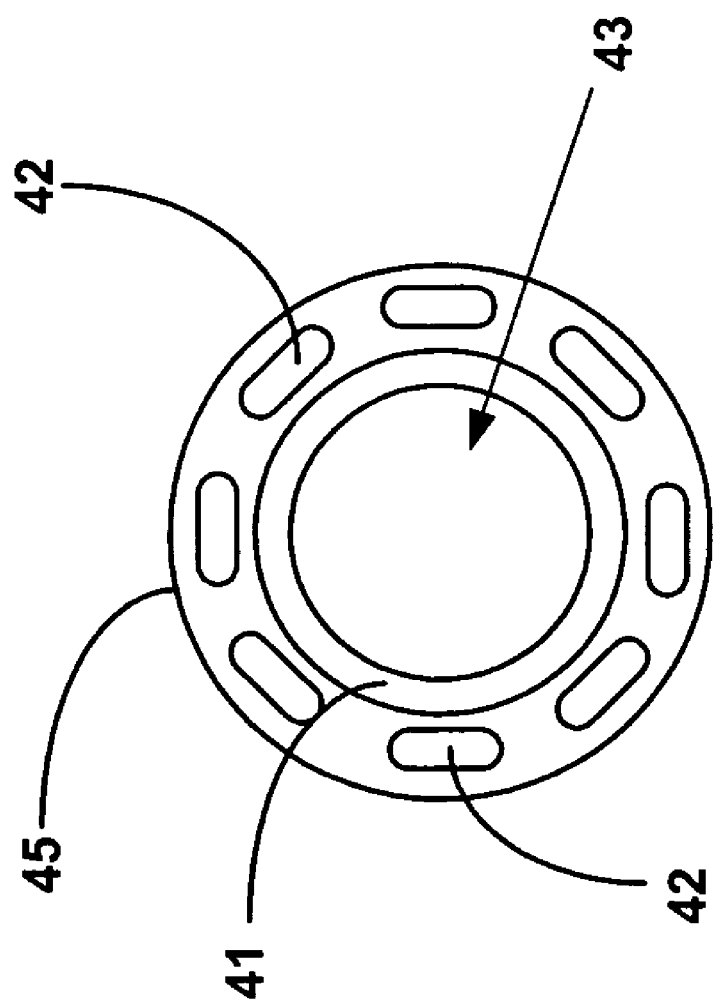
FIG. 8 is a top schematic view of an LED ring light portion of the darkfield illuminator of FIG. 7; and, FIG. 9 is an elevation view of the darkfield illuminator of FIG. 7 as employed with the LED-assisted magnifying device of FIG. 1.

An important feature of darkfield illuminator 36 is an open darkfield cavity 43 internal to canister 45 and having blackened walls so as to enhance the illumination darkfield provided by darkfield illuminator 36. FIG. 7A is a simplified view of portions of FIG. 7 illustrating with dotted arrows how the rim 41 and encasement opening 44 portions of the source of darkfield illumination 39 cooperate with LEDs 42 to provide darkfield illumination onto gemstone 47 at a plurality of different oblique angles, except that no illumination is from directly below gemstone 47. FIG. 8 is a top planar view of canister 45 illustrating the circular array of a plurality of LEDs 42 arrayed equally apart around the perimeter of a canister 45 and the rim 41 provided to block illumination from LEDs 42 from entering darkfield cavity 43. LEDs 42 are preferably either white light LEDs emitting white light in the range of about 400 to 800 nm or LEDs 42 may be yellow light LEDs emitting yellow light having wavelengths in the range of about 585 to 595 nm.

Figure 9:
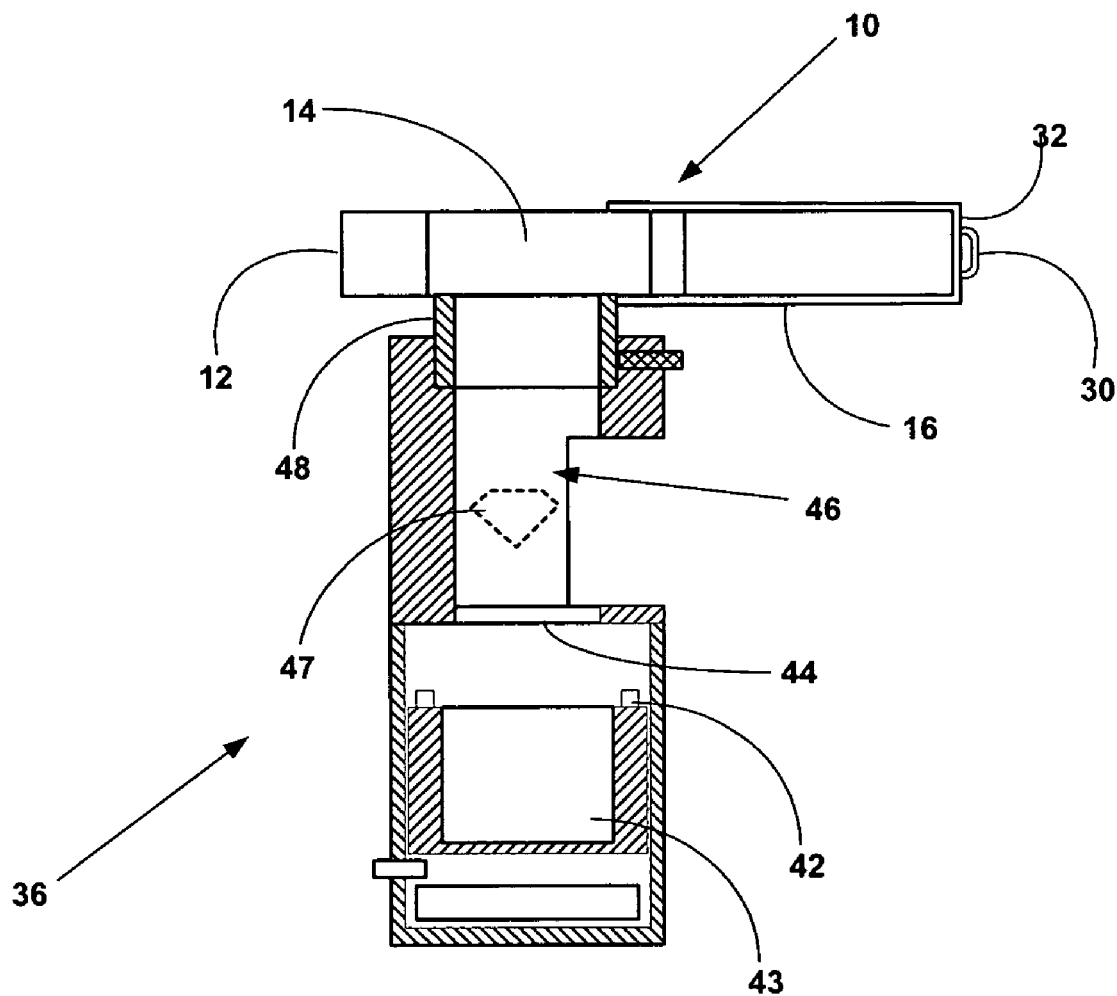

FIG. 9 is an illustration of LED-assisted magnifying device 10 threadably and vertically adjustably attached to darkfield illuminator 36 by means of a threaded screw 48 in a manner so that lens assembly 14, gemstone compartment 46, encasement opening 44, the center of the circular array of LEDs 42, and darkfield cavity 43 are vertically aligned. This arrangement results in minimal direct illumination from LEDs 42 through a gemstone 47 into lens assembly 14 and optimal indirect illumination from LEDs 42 as reflected from the internal surfaces of darkfield cavity 43 and gemstone compartment 46. Consequently, the visibility of inclusion-like defects in gemstones 47 is greatly enhanced in a darkened background. In particular, when gemstones 47 have a very large number of surface facets, as is the case for diamonds, direct inspection using LED-assisted magnifying device 10 without darkfield illuminator 36 is difficult because of very strong direct reflection from facets.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. For example, the shape, size and position of the housing, lens, LEDs, power switches or other structures in the magnifying device of the present invention may be varied without departing from the scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. An article of manufacture comprising:
   a housing;
   a magnifying lens assembly mounted in said housing;
   a generally circularly-shaped array of a plurality of LEDs adapted to produce a uniform pattern of illuminating radiation below said magnifying lens assembly;
   a power source adapted to provide power to said circularly-shaped array of LEDs;
   a power switch adapted to connect said power source to said circularly-shaped array of LEDs; and,
   a darkfield illuminator having a source of darkfield illumination comprising LED light reflected at oblique angles and azimuths inside an open compartment sized to accept gemstones.

2. The article of manufacture of claim 1 wherein the darkfield illuminator comprises an encasement for containing a gemstone, the encasement being attached to the source of darkfield illumination.

3. The article of manufacture of claim 1 wherein the source of darkfield illumination is a circular array of a plurality of LEDs supported atop the perimeter of a cup-like canister and the darkfield effect is generated by a darkfield cavity internal to said canister.

4. The article of manufacture of claim 3 wherein an upwardly extending rim is disposed internally adjacent to the plurality of LEDs atop the cup-like canister blocking illumination for the array of LEDs from entering the darkfield cavity.

5. The article of manufacture of claim 3 wherein the plurality of LEDs comprise LEDs emitting white light or yellow light radiation.

* * * * *